US00PP32661P3

(12) United States Plant Patent
Hofmann

(10) Patent No.: US PP32,661 P3
(45) Date of Patent: Dec. 15, 2020

(54) ***SUTERA* PLANT NAMED 'INSUTSNPIM'**

(50) Latin Name: *Sutera cordata*
Varietal Denomination: INSUTSNPIM

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GMBH + Co. KG, Gensingen (DE)

( * ) Notice: Subject to any disclaimer, the term of this patent is extended or adjusted under 35 U.S.C. 154(b) by 0 days.

(21) Appl. No.: 16/873,439

(22) Filed: Apr. 11, 2020

(65) Prior Publication Data

US 2020/0329622 P1 Oct. 15, 2020

(30) Foreign Application Priority Data

Apr. 15, 2019 (CA) ..... PBR 19-9767

(51) Int. Cl.
*A01H 5/02* (2018.01)
*A01H 6/00* (2018.01)

(52) U.S. Cl.
USPC ..... Plt./485
CPC ..... *A01H 6/00* (2018.05); *A01H 5/02* (2013.01)

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Sutera* plant named 'INSUTSNPIM', characterized by its low mounding to outwardly spreading and trailing plant habit; moderately vigorous growth habit; freely branching habit; dense and bushy plant form; early and freely flowering habit; large light purple-colored flowers with darker purple-colored centers; long flowering season; and good garden performance.

1 Drawing Sheet

Botanical designation: *Sutera cordata.*

Cultivar denomination: 'INSUTSNPIM'.

Cross-Reference to a Related Application and Statement Regarding Prior Disclosures by Inventor/Applicant:

This application claims priority to a Canadian Plant Breeders' Rights application filed on Apr. 15, 2019, application number 19-9767. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Sutera* plant, botanically known as *Sutera cordata* and hereinafter referred to by the name 'INSUTSNPIM'.

The new *Sutera* plant is a product of a planned breeding program conducted by the Inventor in Johannesburg, South Africa. The objective of the breeding program is to create new freely-branching and trailing *Sutera* plants with numerous large flowers and high temperature tolerance.

The new *Sutera* plant originated from a cross-pollination conducted by the Inventor in March, 2016 in Johannesburg, South Africa of a proprietary selection of *Sutera cordata* identified as code number Su15-7305-1, not patented, as the female, or seed, parent with a proprietary selection of *Sutera cordata* identified as code number Su15-7006-1, not patented, as the male, or pollen, parent. The new *Sutera* plant was discovered and selected by the Inventor as a flowering plant from within the progeny of the stated cross-pollination in a controlled greenhouse environment in Johannesburg, South Africa in April, 2018.

Asexual reproduction of the new *Sutera* plant by terminal vegetative cuttings in a controlled greenhouse environment in Gensingen, Germany since April, 2018 has shown that the unique features of this new *Sutera* plant are stable and reproduced true to type in successive generations.

SUMMARY OF THE INVENTION

Plants of the new *Sutera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INSUTSNPIM'. These characteristics in combination distinguish 'INSUTSNPIM' as a new and distinct *Sutera* plant:

1. Low mounding to outwardly spreading and trailing plant habit.
2. Moderately vigorous growth habit.
3. Freely branching habit; dense and bushy plant form.
4. Early and freely flowering habit.

5. Large light purple-colored flowers with darker purple-colored centers.
6. Long flowering season.
7. Good garden performance.

Plants of the new *Sutera* can be compared to plants of the female parent selection. Plants of the new *Sutera* differ primarily from plants of the female parent selection in the following characteristics:

1. Plants of the new *Sutera* are larger than and not as compact as plants of the female parent selection.
2. Plants of the new *Sutera* have larger flowers than plants of the female parent selection.
3. Flowers of plants of the new *Sutera* are light purple in color with darker purple-colored centers whereas flowers of plants of the female parent selection are soft lavender in color.

Plants of the new *Sutera* can be compared to plants of the male parent selection. Plants of the new *Sutera* differ primarily from plants of the male parent selection in the following characteristics:

1. Plants of the new *Sutera* are larger than and not as compact as plants of the male parent selection.
2. Plants of the new *Sutera* are more freely branching than plants of the male parent selection.
3. Flowers of plants of the new *Sutera* are light purple in color with darker purple-colored centers whereas flowers of plants of the male parent selection are lavender in color with pink-colored centers.

Plants of the new *Sutera* can be compared to plants of the *Sutera cordata* 'DANOVA982', disclosed in U.S. Plant Pat. No. 22,398. In side-by-side comparisons, plants of the new *Sutera* differ primarily from plants of 'DANOVA982' in the following characteristics:

1. Plants of the new *Sutera* have larger flowers than plants of 'DANOVA982'.
2. Flowers of plants of the new *Sutera* are light purple in color with darker purple-colored centers whereas flowers of plants of 'DANOVA982' are light violet in color.
3. Plants of the new *Sutera* are more freely flowering and flower more continuously during the summer than plants of 'DANOVA982'.

BRIEF DESCRIPTION OF THE PHOTOGRAPHS

The accompanying colored photographs illustrate the overall appearance of the new *Sutera* plant showing the colors as true as it is reasonably possible to obtain in colored reproductions of this type. Colors in the photographs may differ slightly from the color values cited in the detailed botanical description which accurately describe the colors of the new *Sutera* plant.

At the top of the photographic sheet (FIG. 1) is a side perspective view of a typical flowering plant of 'INSUTSNPIM' grown in a container and at the bottom of the photographic sheet is a close-up view of a typical flowering plant of 'INSUTSNPIM'.

DETAILED BOTANICAL DESCRIPTION

The aforementioned photographs and following observations and measurements describe plants grown during the spring in 15-cm containers in a polyethylene-covered greenhouse in St. Thomas, Ontario, Canada and under cultural practices typical of commercial *Sutera* production. During the production of the plants, day temperatures averaged 27° C. and night temperatures averaged 15° C. Plants were pinched three weeks after propagating rooted cuttings and were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Sutera cordata* 'INSUTSNPIM'.

Parentage:

*Female, or seed, parent*.—Proprietary selection of *Sutera cordata* identified as code number Su15-7305-1, not patented.

*Male or pollen parent*.—Proprietary selection of *Sutera cordata* identified as code number Su15-7006-1, not patented.

Propagation:

*Type*.—By terminal vegetative cuttings.

*Time to initiate roots, summer and winter*.—About seven to ten days at soil temperatures ranging from about 21° C. to 22° C.

*Time to produce a rooted young plant, summer*.—About three to four weeks at soil temperatures ranging from about 21° C. to 22° C.

*Time to produce a rooted young plant, winter*.—About four to five weeks at soil temperatures ranging from about 21° C. to 22° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Low mounding to outwardly spreading and trailing plant habit; moderately vigorous growth habit; moderate growth rate.

*Plant height*.—About 15 cm.

*Plant diameter* (*area of spread*).—About 40.2 cm.

Lateral branch description:

*Branching habit*.—Freely branching habit; when pinched, about four primary lateral branches each with up to ten secondary lateral branches develop per plant; dense and bushy plant form.

*Length, primary laterals*.—About 21.3 cm.

*Diameter, primary laterals*.—About 1.5 mm.

*Internode length*.—About 2.4 cm.

*Strength*.—Moderately strong.

*Aspect*.—Horizontally spreading to trailing.

*Texture and luster*.—Moderately to densely pubescent; matte.

*Color, developing*.—Close to 144B.

*Color, developed*.—Close to 147B.

Leaf description:

*Arrangement*.—Before flowering, alternate; after flowering, opposite, simple.

*Length*.—About 2.1 cm.

*Width*.—About 1.6 cm.

*Shape*.—Broadly elliptic to rounded.

*Apex*.—Acute.

*Base*.—Attenuate.

*Margin*.—Dentate, not lobed.

*Texture and luster, upper and lower surfaces*.—Sparsely pubescent; matte.

*Venation pattern*.—Pinnate, reticulate.

*Color*.—Developing leaves, upper surface: Close to 138A. Developing leaves, lower surface: Close to 138B. Fully expanded leaves, upper surface: Close to 137A; venation, close to 144A. Fully expanded leaves, lower surface: Close to 138A; venation, close to 144B.

*Petioles*.—Length: About 4.8 mm. Diameter: About 2 mm. Strength: Weak. Texture and luster, upper and lower surfaces: Moderately pubescent; matte. Color, upper surface: Close to 137A. Color, lower surface: Close to 147B.

Flower description:

*Flower arrangement*.—Large single salverform flowers; freely flowering habit with potentially about 529 flower buds and open flowers per plant at one time; flowers face mostly upright then turning outwardly.

*Fragrance*.—None detected.

*Flowering habit*.—Early flowering habit, plants begin flowering about five weeks after planting; long flowering season, plants flower continuously from the spring until the autumn in Southern Ontario.

*Flower longevity*.—Flowers last about five days on the plant; flowers not persistent.

*Flower diameter*.—About 2.5 cm.

*Flower length* (*height*).—About 1.1 cm.

*Throat diameter*.—About 5 mm.

*Tube length*.—About 1 cm.

*Tube diameter, base*.—About 1.5 mm.

*Flower buds*.—Length: About 12 mm. Diameter: About 7 mm. Shape: Obovate. Texture and luster: Densely pubescent; matte. Color: Close to 75C.

*Petals*.—Quantity and arrangement: Five per flower in a single whorl; fused at the base. Lobe length: About 1 cm. Lobe width: About 1 cm. Lobe shape: Roughly orbicular. Lobe apex: Obtuse, rounded. Lobe margin: Entire; slightly undulate. Texture and luster, petal lobes, upper surface: Smooth, glabrous; matte. Texture and luster, petal lobes, lower surface: Moderately pubescent; matte. Texture and luster, throat: Sparse to moderately pubescent, matte. Texture and luster, tube: Moderately to densely pubescent, matte. Color: Petal lobes, when opening, upper surface: Close to 75C; towards the base, close to N78C. Petal lobes, when opening, lower surface: Close to 69B; towards the base, close to 76A. Petal lobes, fully opened, upper surface: Close to 84C; towards the base, close to N78B; venation, similar to lamina; color does not change with development. Petal lobes, fully opened, lower surface: Close to 84C; towards the base, close to 84B; venation, similar to lamina; color does not change with development. Throat: Close to 17A to 17B. Tube: Close to 150D.

*Sepals*.—Quantity and arrangement: Five per flower in a single whorl; fused at the base; calyx, star-shaped. Length: About 8 mm. Width: About 1 mm. Shape: Lanceolate to linear. Apex: Acute. Margin: Entire. Texture and luster, upper surface: Sparsely pubescent; matte. Texture and luster, lower surface: Moderately pubescent; matte. Color: When opening, upper and lower surfaces: Close to 144A. Fully opened, upper and lower surfaces: Close to 146A.

*Peduncles*.—Length: About 13.2 cm. Diameter: About 0.6 mm. Angle: About 30° from vertical. Strength: Moderately strong. Texture and luster: Moderately to densely pubescent; matte. Color: Close to 137B.

*Reproductive organs*.—Androecium: Quantity of stamens per flower: About four. Filament length: About 8 mm. Filament color: Close to 157D. Anther size: About 2 mm by 1 mm. Anther shape: Oval. Anther color: Close to 13B. Amount of pollen: Moderate. Pollen color: Close to 14A. Gynoecium: Quantity of pistils per flower: One. Pistil length: About 1.2 cm. Style length: About 9 mm. Style color: Close to 145C. Stigma size: About 1 mm by 3 mm. Stigma shape: Lanceolate. Stigma color: Close to 144A. Ovary color: Close to 144A.

*Seeds and fruits*.—To date, seed and fruit production have not been observed on plants of the new *Sutera*.

Garden performance: Plants of the new *Sutera* have been observed to have good garden performance and to tolerate wind, rain and to be suitable for USDA Hardiness Zones 9 to 11.

Pathogen & pest tolerance: To date, plants of the new *Sutera* have not been observed to be tolerant to pathogens and pests common to *Sutera* plants.

It is claimed:

1. A new and distinct *Sutera* plant named 'INSUTSNPIM' as illustrated and described.

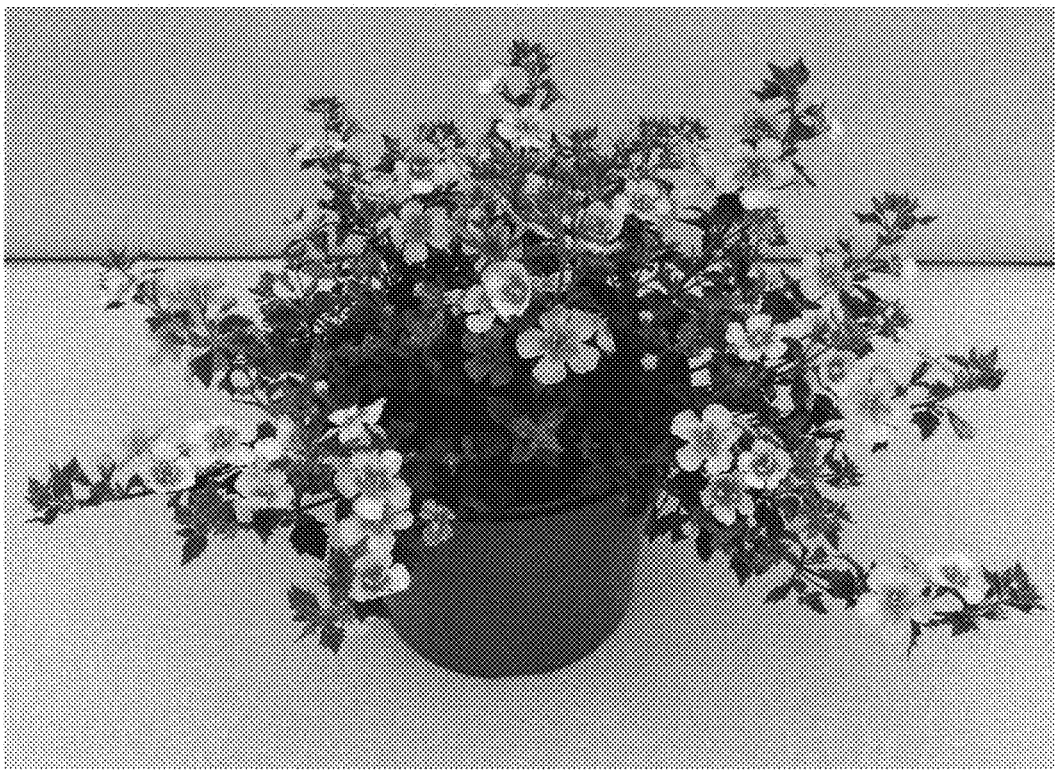
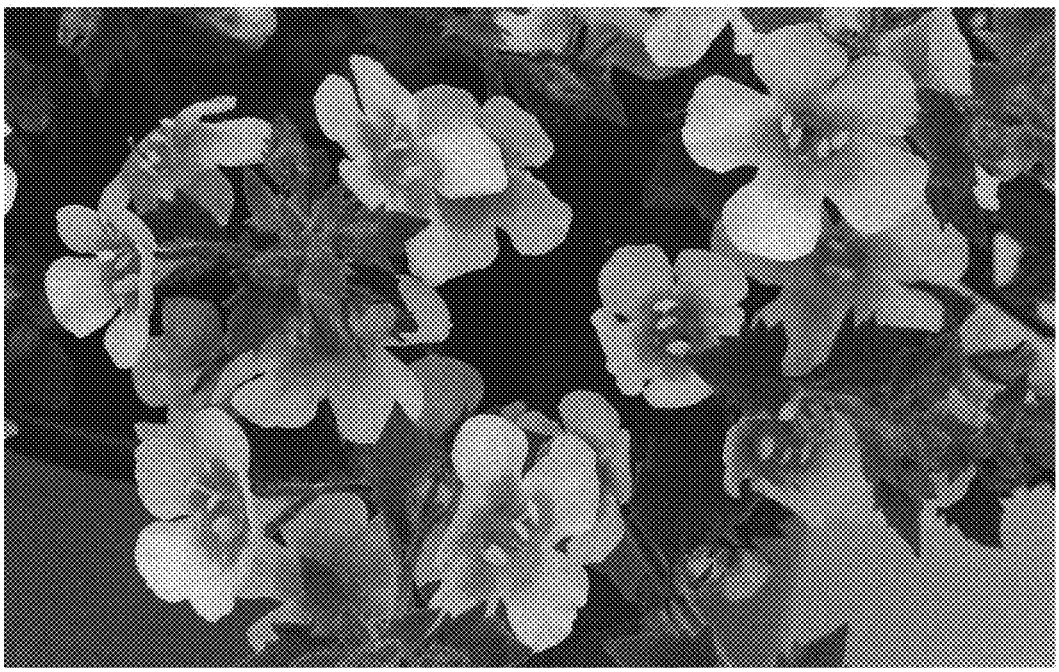

* * * * *